United States Patent
Merrill et al.

(10) Patent No.: US 6,864,399 B2
(45) Date of Patent: Mar. 8, 2005

(54) SILICA-SUPPORTED ALKYLATION CATALYST

(75) Inventors: James T. Merrill, Katy, TX (US); James R. Butler, Houston, TX (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 10/193,792

(22) Filed: Jul. 12, 2002

(65) Prior Publication Data

US 2002/0198424 A1 Dec. 26, 2002

Related U.S. Application Data

(63) Continuation of application No. 09/691,675, filed on Oct. 18, 2000, now abandoned.

(51) Int. Cl.⁷ .................................................. C07C 2/66
(52) U.S. Cl. ....................................... 585/467; 585/446
(58) Field of Search .................................. 585/446, 467

(56) References Cited

U.S. PATENT DOCUMENTS

| | | | | |
|---|---|---|---|---|
| 5,227,558 A | * | 7/1993 | Shamshoum et al. | 585/446 |
| 5,792,894 A | * | 8/1998 | Huff, Jr. et al. | 585/446 |
| 5,907,073 A | * | 5/1999 | Ghosh | 585/467 |

FOREIGN PATENT DOCUMENTS

| | | | | |
|---|---|---|---|---|
| EP | 432814 A1 | * | 6/1991 | B01J/29/28 |
| EP | 507761 A1 | * | 10/1992 | B01J/29/28 |

* cited by examiner

*Primary Examiner*—Walter D. Griffin
(74) *Attorney, Agent, or Firm*—Madan, Mossman & Sriram

(57) ABSTRACT

The alkylation of benzene-containing feedstock over a zeolite beta alkylation catalyst which is formulated with a silica binder and has an average regeneration coefficient of at least 95% for at least three regenerations. The alkylation reaction is carried out in the liquid phase or supercritical region with a $C_2$–$C_4$ alkylating agent, specifically ethylene. The catalyst exhibits a regeneration coefficient of at least 95% after ethylation of the benzene with ethylene at a benzene/ethylene mole ratio of less than 10. The ethylation of benzene occurs at an initial designated primary activity. The operation of the reaction zone is continued until the activity of the catalyst for the ethylation of benzene decreases by a value of at least 0.1% and not more 1% from the initial designated primary activity. The operation of the reaction for alkylation is terminated and a regeneration procedure is instituted in which the catalyst is regenerated in an oxidizing environment at an average temperature of no more than 500° C. At the conclusion of the regeneration procedure, the operation of the alkylation zone is reinstituted with the reaction zone again operated under conditions as described above followed by regeneration.

8 Claims, 2 Drawing Sheets

SILICA-SUPPORTED ALKYLATION CATALYST

This is a continuation of prior U.S. application Ser. No. 09/691,675 filed Oct. 18, 2000, now abandoned.

FIELD OF THE INVENTION

This invention involves an aromatic alkylation process involving alkylation of an aromatic substrate such as benzene over a zeolite beta aromatic alkylation catalyst formulated with a silica binder.

BACKGROUND OF THE INVENTION

Zeolite beta is a well known molecular sieve catalyst which has been employed in hydrocarbon conversion processes such as dewaxing and the catalytic cracking of relatively heavy high molecular weight hydrocarbon oils. Zeolite beta, as employed in such conversion practices, was first disclosed in U.S. Pat. No. 3,308,069 to Wadlinger et al and later in a so-called improved form in U.S. Pat. No. 4,642,226 to Calvert et al. As disclosed in the patent to Calvert, among the conversation processes in which zeolite beta is particularly useful are dewaxing, hydroisomerization, cracking, hydrocracking, and aromatization through the conversion of light aliphatic hydrocarbons to aromatic hydrocarbons. As disclosed in Calvert, the zeolite beta employed in such conversion processes can be prepared by synthesis procedures involving the hydrothermal digestation of reaction mixtures, including silica, alumina, various other optional metal oxides or hydroxides, and an organic templating agent which is employed to produce the desired crystalline structure. The amount of silica and alumina in the reaction mixture may vary with a silica to alumina mole ratio in the range of 20–250, resulting ultimately in silica/alumina mole ratios of the crystalline product, ranging from less than 20 to about 60 to as high as, in one example given in Calvert, 171.

Molecular sieve catalyst, such as zeolite beta as well as numerous other molecular sieves, are commonly employed in combination with a matrix material which acts as a binder for the molecular sieve. For example, the aforementioned patent to Wadlinger discloses that the zeolite beta can be employed alone or as a dispersed mixture in combination with a low activity and/or catalytically active material which serves as a binder for the zeolite catalyst constituent. The aforementioned patent to Calvert discloses the use of inorganic materials such as clay, silica, or alumina or various composite materials such as silica/alumina, silica/magnesia, and various other binary and trinary compositions.

In addition to the use of zeolite beta in hydrocarbon conversion processes, including, for example, dewaxing, hydrocracking, or aliphatic aromatic conversation as described above, zeolite beta, as well as numerous other molecular sieves, has also been employed as a catalyst in the alkylation of an aromatic substrate. Such alkylation conversion reactions include the alkylation of aromatic substrates such as benzene to produce alkyl aromatics such as ethylbenzene, ethyltoluene, cumene or higher aromatics and the transalkylation of polyalkyl benzenes to monoalkyl benzenes. Typically, an alkylation reactor which produces a mixture of mono- and poly-alkyl benzenes may be coupled through various separation stages to a downstream transalkylation reactor. Such alkylation and transalkylation reactions can be carried out in the liquid phase, in the vapor phase or under conditions in which both liquid and vapor phases are present.

U.S. Pat. No. 4,185,040 to Ward et al discloses an alkylation process employing a molecular sieve catalyst of low sodium content, less than 0.5 wt. % $Na_2O$, which is said to be especially useful in the production of ethylbenzene from benzene and ethylene and cumene from benzene and propylene. Examples of suitable zeolites include molecular sieves of the X, Y, L, B, ZSM-5, and omega crystal types, with steam stabilized hydrogen Y zeolite being preferred. Specifically disclosed is a steam stabilized ammonium Y zeolite containing about 0.2% $Na_2O$. Various catalyst shapes are disclosed in the Ward et al patent. While cylindrical extrudates may be employed, a particularly preferred catalyst shape is a so-called "trilobal" shape which is configured somewhat in the nature of a three leaf clover. The surface area/volume ratio of the extrudate should be within the range of 85–160 in.$^{-1}$. The alkylation process may be carried out with either upward or downward flow, the latter being preferred, and preferably under temperature and pressure conditions so that at least some liquid phase is present, at least until substantially all of the olefin alkylating agent is consumed. The Ward et al patent states that rapid catalyst deactivation occurs under most alkylating conditions when no liquid phase is present. In the Ward process, as well as in the various conversion processes described previously, the zeolite may be incorporated with a porous mineral oxide binder to arrive at the particulate catalyst configuration such as the trilobal configuration. Thus, Ward discloses the use of alumina gel, silica gel, silica/alumina co-gels, various clays, titania, and other mineral oxides with alumina being preferred for use in combination with the preferred zeolite-Y.

As is the case with zeolite employed in conversion processes or in alkylation processes, procedures involving zeolite beta for alkylation or transalkylation processes are normally carried out employing alumina as a binder providing a matrix for the zeolite catalyst. Thus, U.S. Pat. No. 4,891,458 to Ennes et al discloses a process for the liquid phase alkylation or transalkylation of an aromatic hydrocarbon employing a zeolite beta catalyst. The zeolite beta is disclosed in Ennes et al to have a silicon to aluminum atomic ratio of greater than 5:1 and less than 100:1 and preferably greater than 5:1 and less than 50:1. Ennes discloses alkylation under conditions in which the mole ratio of aromatics to olefins is at least 4 to 1 in order to prevent rapid catalyst fouling. The reaction temperature ranges from about 100° to 600° F. and the reaction pressure is typically about 50–100 psig and sufficient to maintain at least a partial liquid phase. Preferably the zeolite beta used in the Ennes procedure is predominantly in the hydrogen form, arrived at by ammonium exchange of the synthesized product followed by calcination. Innes discloses that the pure zeolite may be employed with an inorganic oxide binder, such as alumina, silica, silica/alumina, or naturally-occurring clays. Innes continues that the preferred inorganic binder is alumina.

Another alkylation procedure is disclosed in U.S. Pat. No. 4,798,816 to Ratcliffe et al and involves the use of molecular sieve alkylation catalysts which have been treated in a manner to improve selectivity to monoalkylation, specifically in the propylation of benzene to produce cumene. Selectivity is increased by at least one percentage point by first depositing a carbonaceous material on the catalyst and then subjecting the resultant carbon containing catalyst particles to combustion. Specific zeolitic crystalline molecular sieves include those selected from the group of Y zeolites, fluorided Y zeolites, X zeolites, zeolite beta, zeolite L, and zeolite omega. The preferred Y-type zeolites may be dealuminated to produce an overall silica to alumina ratio above 6. As is the case in the previous references, the preferred inorganic refractory oxide material used as a binder is alumina, specifically catapal, although other binders such as alumina, gallia, thallia, titania, zirconia, beryllia, silica, silica-alumina, and various other materials are disclosed.

EPA publication 467,007 to Butler discloses other processes having separate alkylation and transalkylation zones employing various molecular sieve catalysts and with the output from the transalkylation reactor being recycled to an intermediate separation zone. Here, a benzene separation zone, from which an ethylbenzene/polyethylbenzene fraction is recovered from the bottom with recycling of the overhead benzene fraction to the alkylation reactor, is preceded by a prefractionation zone. The prefractionation zone produces an overhead benzene fraction which is recycled along with the overheads from the benzene column and a bottom fraction which comprises benzene, ethylbenzene and polyethylbenzene. Two subsequent separation zones are interposed between the benzene separation zone and the transalkylation reactor to provide for recovery of ethylbenzene as the process product and a heavier residue fraction. The polyethylbenzene fraction from the last separation zone is applied to the transalkylation reactor and the output there is applied directly to the second benzene separation column or indirectly through a separator and then to the second benzene separation column. Butler discloses that the alkylation reactor may be operated in the liquid phase with a catalyst such as zeolite-beta, zeolite-Y or zeolite-omega or in the vapor phase, employing a catalyst such as silicalite or ZSM-5.

Another procedure involving the liquid phase alkylation of an aromatic substrate is disclosed in EPA Publication No. 507,761 to Shamshoum et al. This procedure involves the use of a molecular sieve catalyst which is based upon zeolite beta but which has been modified by the incorporation of lanthanum. The lanthanum-modified zeolite beta catalyst is disclosed in Shamshoum et al to provide little or no xylene make under the mild liquid phase alkylation conditions as contrasted with the use of zeolite beta in the hydrogen form. In the Shamshoum et al procedure, the initial zeolite beta preferably has a silica/alumina ratio of between 20 to 50, which is initially subject to an ion exchange step followed by calcination at a temperature of about 570° C. for 2 or more hours. After subsequent ion exchange and calcination procedures, the molecular sieve is dried followed by incorporation of lanthanum into the zeolite system by ion exchange with a lanthanum salt solution. Shamshoum et al disclosed that the lanthanum beta zeolite is mixed with a binder, such as alumina sol, gamma alumina, or other refractory oxides, to produce a zeolite binder mixture which is then pelletized.

Other procedures involving liquid phase alkylation of benzene are disclosed in U.S. Pat. Nos. 5,030,786 to Shamshoum et al, and 5,073,653 to Butler. Shamshoum '786 discloses the use of molecular sieves having a pore size greater than 6.5 angstroms, specifically zeolites Y and beta having a pore size within the range of 7–7.5 angstroms. The patent to Butler discloses alkylation of benzene in the liquid phase employing catalysts including zeolites, such as zeolite omega, zeolite beta, and zeolite Y. Butler discloses that the operation of the alkylation reactors under relatively mild liquid phase conditions enables the use of relatively low benzene-ethylene mole ratios over the reactor of about 5:1 or less and preferably 4:1 or less down to about 2:1. Higher ratios up to 15:1 are also disclosed. Butler specifically discloses a catalyst containing 80% crystalline zeolite omega and 20 wt. % alumina binder.

SUMMARY OF THE INVENTION

In accordance with the present invention there is provided an aromatic alkylation process for the alkylation of benzene containing feed stock over a zeolite beta alkylation catalyst. The zeolite beta alkylation catalyst is formulated with a silica binder and has an average regeneration coefficient of at least 95% for at least three regenerations. The alkylation reaction is carried out in the liquid phase or supercritical region with a $C_2$–$C_4$ alkylating agent. In a preferred embodiment of the invention, the alkylating agent is an ethylating agent, more specifically ethylene. The catalyst exhibits a regeneration coefficient of at least 95% after ethylation of the benzene with ethylene at a benzene/ethylene mole ratio of less than 10.

In a further aspect of the invention a feed stock containing benzene is supplied into a reaction zone containing a molecular sieve catalyst comprising a zeolite beta alkylation catalyst formulated with a silica binder. Ethylene is supplied to the reaction zone which is operated under temperature and pressure conditions in which benzene is in the liquid phase or in the supercritical phase. The ethylation of benzene occurs at an initial designated primary activity. The operation of the reaction zone is continued until the activity of the catalyst for the ethylation of benzene decreases by a value of at least 0.1% from the initial designated primary activity. This decrease in value should not exceed 1% from the initial designated primary activity. The operation of the reaction for alkylation is terminated and a regeneration procedure is instituted. In the regeneration procedure the catalyst is regenerated in an oxidizing environment at an average temperature of no more than 500° C. At the conclusion of the regeneration procedure, the operation of the alkylation zone is reinstituted with the reaction zone again operated at temperature and pressure conditions effective to cause ethylation of the benzene in the liquid phase or in the supercritical phase. The initial activity of the catalyst in the second pass is such as to provide a secondary activity at least 95% of the initial primary activity. The operation of the alkylation reaction zone continues until the activity of the catalyst declines in an amount of at least 0.1% of the initial secondary activity and the operation of the alkylation reaction zone is again terminated and the catalyst is subjected to a regeneration procedure as described above. At the conclusion of the regeneration procedure, benzene and ethylene are again supplied to the alkylation reaction zone. The alkylation zone is operated under the temperature and pressure in which benzene is in the liquid phase or in the supercritical phase to provide an additional tertiary activity for the ethylation of benzene of at least 95% of the secondary activity.

DETAILED DESCRIPTION OF THE INVENTION

Figure 1:
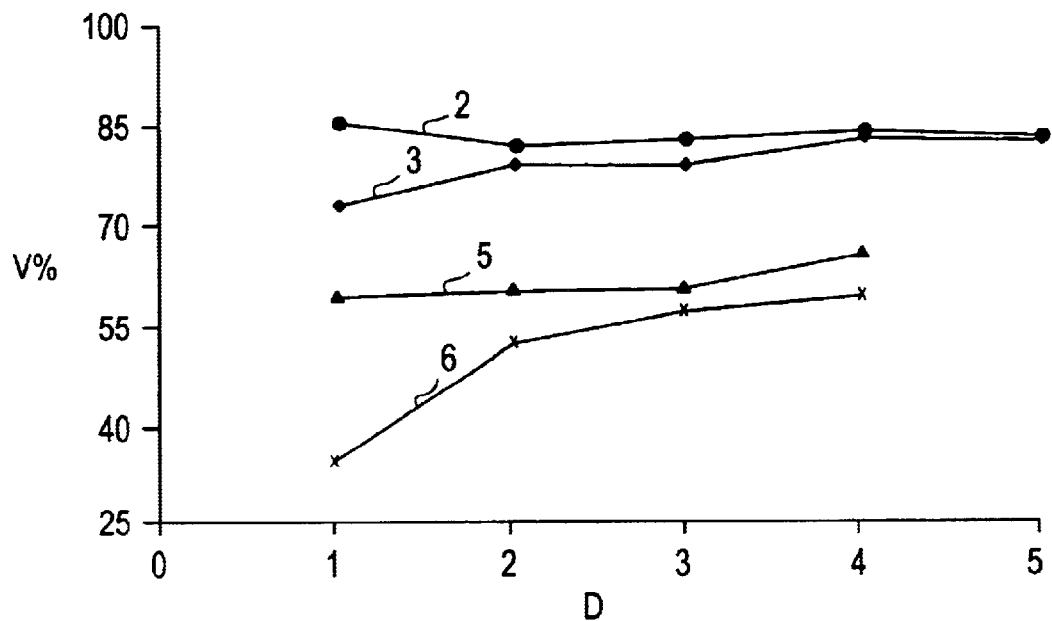
FIG. 1 is a graph illustrating the volume percent of a catalyst bed at maximum temperature under liquid phase alkylation conditions employing a zeolite beta catalyst formulated with an alumina binder.

The present invention involves alkylation of an aromatic substrate comprising benzene in a reaction zone containing a zeolite beta alkylation catalyst which preferably is carried out under relatively mild liquid phase alkylation conditions. The invention is especially applicable to the ethylation of benzene under mild liquid phase conditions producing little or no xylenes and the invention will be described specifically by reference to the production of ethylbenzene. However, other alkylation reactions may be utilized in carrying out the invention. For example, the invention may be applied to the reaction of propylene with benzene to produce cumene. Also, while olefinic alkylating agents normally will be employed, other alkylating agents such as alkynes, alkyl halides, alcohols, ethers, and esters as disclosed, for example in U.S. Pat. No. 3,551,510 to Pollitzer et al. may be used.

As indicated above, the alkylation reactor is preferably operated under relatively mild pressure and temperature conditions in which the benzene is in the liquid phase, that is, at a temperature of well below the critical temperature of benzene, and under pressure sufficient to maintain the benzene in the liquid phase. However, the alkylation reaction can be carried out under conditions in which the benzene is in the supercritical phase, ie. at temperature and pressure conditions above the critical temperature and pressure, and unless otherwise indicated in the context, the terms "liquid phase" or "liquid phase reaction" as used here will be understood to denote operation in the supercritical region as well as in the liquid region.

The zeolite beta employed in the present invention can be conventional zeolite beta, or it may be a modified zeolite beta of any one of various types described in greater detail below. Regardless of the nature of the zeolite beta, the present invention proceeds in a manner contrary to the conventional procedure in which zeolite beta is normally mulled with an alumina binder such as gamma alumina or catapal alumina. Thus, as described in greater detail below, the zeolite beta employed in the present invention is formulated with a silica binder which results in a zeolite beta catalyst for use in liquid phase alkylation, which exhibits substantially better deactivation and regeneration characteristics than zeolite beta formulated with a conventional alumina binder. The zeolite beta formulated with a silica binder has a regeneration characteristic as described below after at least three regenerations which is at least 105% of the regeneration coefficient of the zeolite beta catalyst formulated with an alumina binder with the alumina binder being in the same amount as the silica binder employed in the catalyst.

The zeolite beta employed in the present invention can be a high silica/alumina ratio zeolite beta, a lanthanum-modified zeolite beta, or a ZSM-12 modified zeolite beta as described in detail below. It also can, of course, be a more or less conventional zeolite beta as disclosed, for example, in the aforementioned U.S. Pat. Nos. 3,308,609 to Wadlinger et al and 4,642,226 to Calvert et al. Regardless of the nature of the zeolite beta, it is formulated with a silica binder to provide a catalyst which is substantially more stable than zeolite beta formulated with an alumina binder in the traditional manner. In addition, the zeolite beta-silica-bound catalyst of the present invention is stable at substantially lower benzene/ethylene ratios than is the case with corresponding zeolite beta catalyst formulated with an alumina binder.

Zeolite beta is, as noted previously, a well-known molecular sieve catalyst and basic procedures for its preparation are well known to those skilled in the art. Procedure for preparation of crystalline zeolite beta are disclosed in the aforementioned U.S. Pat. Nos. 3,308,069 to Wadlinger et al and 4,642,226 to Calvert et al and European Patent Publication No. 159,846 to Reuben, the entire disclosures of which are incorporated herein by reference. The zeolite beta can be prepared to have a low sodium content, i.e. less than 0.2 wt. % expressed as $Na_2O$ and the sodium content can be further reduced to a value of about 0.02 wt. % by an ion exchange treatment.

As disclosed in the above-referenced U.S. patents to Wadlinger et al., and Calvert et al, zeolite beta can be produced by the hydrothermal digestion of a reaction mixture comprising silica, alumina, sodium or other alkyl metal oxide, and an organic templating agent. Typical digestion conditions include temperatures ranging from slightly below the boiling point of water at atmospheric pressure to about 170° C. at pressures equal to or greater than the vapor pressure of water at the temperature involved. The reaction mixture is subjected to mild agitation for periods ranging from about one day to several months to achieve the desired degree of crystallization to form the zeolite beta. The resulting zeolite beta is normally characterized by a silica to alumina molar ratio (expressed as $SiO_2/Al_2O_3$) of between about 20 and 50.

The zeolite beta is then subjected to ion-exchange with ammonium ions at uncontrolled pH. It is preferred that an aqueous solution of an inorganic ammonium salt, e.g., ammonium nitrate, be employed as the ion-exchange medium. Following the ammonium ion-exchange treatment, the zeolite beta is filtered, washed and dried, and then calcined at a temperature between about 530° C. and 580° C. for a period of two or more hours.

Zeolite beta can be characterized by its crystal structure symmetry and by its x-ray diffraction patterns. Zeolite beta is a molecular sieve of medium pore size, about 5–6 angstroms, and contains 12-ring channel systems. Zeolite beta is of tetragonal symmetry $P4_122$, a=12.7, c=26.4 Å (W. M. Meier and D. H. Olson Butterworth, Atlas of Zeolite Structure Types, Heinemann, 1992, p. 58); ZSM-12 is generally characterized by monoclinic symmetry. The pores of zeolite beta are generally circular along the 001 plane with a diameter of about 5.5 angstroms and are elliptical along the 100 plane with diameters of about 6.5 and 7.6 angstroms. Zeolite beta is further described in Higgins et al, "The framework topology of zeolite beta," Zeolites, 1988, Vol. 8, November, pp. 446–452, the entire disclosure of which is incorporated herein by reference.

The zeolite beta formulation employed in carrying out the present invention may be based upon conventional zeolite beta such as disclosed in the aforementioned patent to Calvert et al or a lanthanum-modified zeolite beta such as disclosed in the aforementioned EPA publication to Shamshoum et al, or it may be a zeolite beta modified by an intergrowth of ZSM-12 crystals, as disclosed in U.S. Pat. No. 5,907,073 to Ghosh. However, rather than the use of an alumina binder as disclosed in Ghosh, a silica binder as described herein is employed. For a further description of procedures for producing zeolite beta useful in accordance with the present invention, reference is made to the aforementioned U.S. Pat. Nos. 3,308,069 to Wadlinger, 4,642,226 to Calvert, and 5,907,073 to Ghosh and EPA Publication No. 507,761 to Shamshoum, the entire disclosures of which are incorporated herein by reference.

The present invention can also be carried out with a silica-bound zeolite beta based upon a zeolite beta having a higher silica/alumina ratio than that normally encountered. For example, as disclosed in EPA Publication No. 186,447 to Kennedy, a calcined zeolite beta can be dealuminated by a steaming procedure in order to enhance the silica/alumina ratio of the zeolite. Thus, as disclosed in Kennedy, a calcined zeolite beta having a silica/alumina ratio of 30:1 was subjected to steam treatment at 650° C. and 100% steam for 24 hours at atmospheric pressure. The result was a catalyst having a silica/alumina ratio of about 228:1 which was then subjected to an acid washing process to produce a zeolite beta of 250:1. Various zeolite betas, such as described above, can be subject to extraction procedures in order to extract aluminum from the zeolite beta framework by extraction with nitric acid. Acid washing of the zeolite beta is carried out initially to arrive at a high silica/alumina ratio zeolite beta. This is followed by ion-exchanging lanthanum into the zeolite framework. There should be no subsequent acid washing in order to avoid removing lanthanum from the zeolite.

In aromatic alkylation procedures it is highly desirable to regenerate the catalyst after its activity decreases with time in the course of the alkylation procedure. In experimental work carried out respecting the invention, zeolite beta formulated with a silica binder was found to have substantially better regenerability than zeolite beta formulated with an alumina binder in accordance with conventional prior art procedures. Typically, in the course of an alkylation procedure, fresh catalysts will exhibit an initially relatively high activity which can be measured in terms of the percent of ethylbenzene produced at a designated benzene/ethylene mole ratio and benzene space velocity. Desirably, the activity will remain relatively constant during an initial period, but at some point, due to coking of the catalyst in the alkylation procedure, the activity of the catalyst progressively declines. After the catalyst activity declines to a level where further operations are not feasible, or at least not economically practical, the reactor can be taken off stream and the catalyst subject to a regeneration procedure. A typical regeneration procedure involves the initial injection of nitrogen followed by progressively increasing an amount of air added to the nitrogen until a desired oxygen content is reached. For example, an initial oxygen content may be about 0.5 vol./% with the regeneration gas injected at a temperature of about 500° C. As the oxygen content is progressively increased, the coke is burned off of the catalyst until the catalyst reaches a regenerated state in which its activity is near or sometimes even equal to the initial catalyst activity. In the regeneration of zeolite beta, it is desirable to initially provide a nitrogen atmosphere at a temperature near 500° C. in order to drive substantially all of the hydrogen out of the catalyst before the introduction of the oxygen in order to avoid the generation of water.

The regenerability of the catalyst can be characterized in terms of a regeneration coefficient which indicates the level to which the catalyst can be regenerated (compared in terms of its initial activity) from one alkylation pass to another. Thus, considering multiple alkylation and regeneration passes, if the catalyst exhibits an activity under a standard set of conditions of 10% ethylbenzene during a first pass, if the activity of the catalyst at the conclusion of a first regeneration step is 9% ethylbenzene under the same conditions at the start of the second alkylation pass, the regeneration coefficient will be characterized as 90%. If this same regeneration coefficient is observed in going from the second pass with an intervening second regeneration to a third alkylation pass, the initial activity at the start of the third pass would be 8.1% ethylbenzene.

In describing the present invention, the term "regeneration coefficient" will be characterized in terms of the following standard conditions. The catalyst is employed in a liquid phase alkylation procedure carried out at a temperature and pressure of 300° C. and 650 psig at a benzene/ethylene mole ratio of 10. The ethylation reaction is carried out until the activity of the catalyst, as measured by the percent ethylene conversion, declines by 0.5 percent. The catalyst is then regenerated by initially injecting nitrogen for a period of 24 hours at a temperature of 500° C. followed by slowly increasing the oxygen content of the nitrogen to 10% oxygen over a period of 24 hours. The initial activity of the catalyst on a second alkylation pass is then measured in order to arrive at the secondary alkylation activity used to measure the regeneration coefficient.

In experimental work respecting the invention, alkylation was carried out employing a lanthanum beta zeolite formulated with an alumina binder (Catalyst A) and formulated with a silica binder (Catalyst B). The lanthanum beta zeolite was prepared in accordance with the procedure of EPO 507761 and had a silica/alumina ratio of about 100 and a lanthanum content of about 1 wt. %. The experimental work was carried out in a single pass reactor at a temperature of 300° C. and a pressure of 650 psig. The benzene feed had a purity of about 99% and was introduced at a space velocity (LHSV) of 70 $hr^{-1}$. Two sets of tests were carried out, one employing 5 ml. of catalysts in the catalyst bed and the other employing 10 ml. of catalysts in the catalyst bed.

In an initial set of tests carried out employing Catalyst A (the lanthanum beta with an alumina binder), the temperature of the catalyst bed was measured as a function of time for two successive passes with an intervening regeneration procedure. One set of tests was carried out for the 5 ml. catalyst bed and another for the 10 ml. activity.

Alkylation runs were carried out for five days for the 5 ml. catalyst bed and four days for the 10 ml. catalyst bed with the temperature detected by thermocouples spaced along the bed. The results of a first screening test carried with Catalyst A are indicated in FIG. 1 in which the volume percent of the bed at the maximum temperature (490° C.), V, is plotted on the ordinate versus the time of the run in days (D) plotted on the abscissa. In FIG. 1, the curve 2 shows the results for the first pass for the 5 ml. bed and curve 3 shows the results of the second pass for the 5 ml. bed. Curves 5 and 6 show the results for the first and second passes, respectively, through the 10 ml. bed. The temperature was controlled at the maximum of 490° C. during regeneration. For both the 5 ml. and 10 ml. test runs, the lanthanum beta showed a higher rate of deactivation after one regeneration than initially observed. Further, after a second regeneration, no activity was recovered, indicating that the lanthanum beta zeolite formulated with the alumina binder was not sufficiently stable to withstand multiple regenerations.

A second suite of experiments was carried out under critical phase conditions employing the lanthanum beta with a silica binder in the amount of 20%, roughly the same amount of binder employed in the lanthanum beta alumina catalyst composition. Here, the alkylation run was carried out above the critical temperature (289° C.) of benzene. The temperature of the reactor was 300° C., the pressure 650 psig, and the benzene space velocity (LHSV) 70 $hrs.^{-1}$. The catalyst was found to be stable at a benzene/ethylene mole ratio of 10:1. At the conclusion of an initial run carried out for 4 days, the catalyst was regenerated using the following regeneration procedure:

1. Allowing cooling until ambient under a minimum flow of benzene;

2. Begin purge with 240 sccm of nitrogen; maintain reactor in downflow mode;

3. Ramp the temperature at less than 100° C./hr to 400° C. and hold for 3 hours;

4. Cool to 250° C.;

5. Slowly add air at minimal Mass Flow Controller rate; do not allow the exotherm to exceed 490° C.

6. Once the initial rapid burn has completed, slowly increase the air over a 2-hour period to 240 sccm while decreasing the nitrogen to 0 sccm;

7. Raise the temperature to 485° C. and hold for 3 hours; and

8. Cool to ambient temperature with flowing air.

Figure 2:
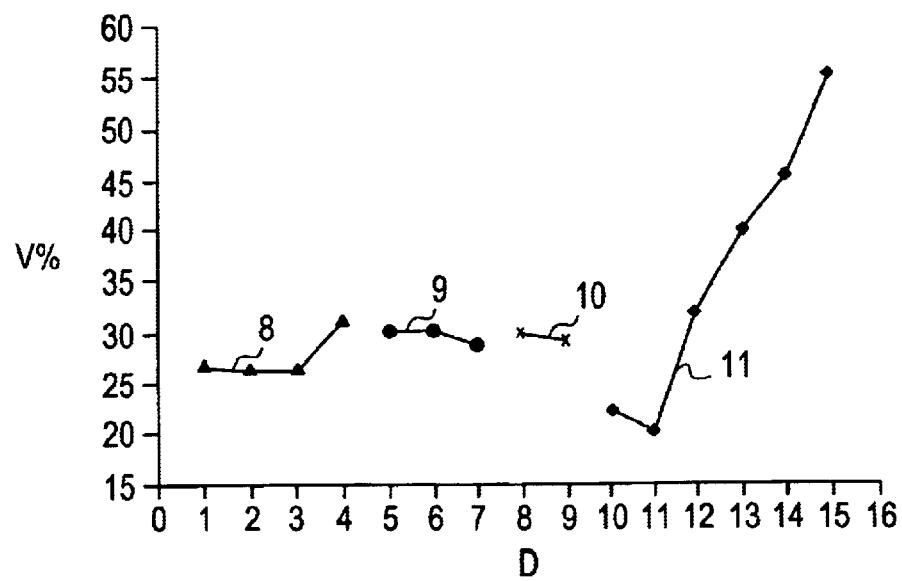
FIG. 2 is a graph illustrating the volume percent of catalyst bed at maximum alkylation temperature employing a regenerated zeolite beta catalyst formulated with a silica binder progressively under liquid phase conditions at progressively decreasing benzene/ethylene mole ratios.

A second pass run was then carried out employing the regenerated catalyst with the benzene rate maintained at a space velocity of 70 hrs.$^{-1}$, and the ethylene rate was progressively increased with time to produce benzene/ethylene ratios of 20:1, 10:1, and 7.9:1. The results of this experimental work are depicted in FIG. 2 in which the volume percent of the bed, V, at the maximum temperature (490° C.) is plotted on the ordinate versus the days, D, on stream for the catalyst bed on the abscissa. In FIG. 2, curve 8 depicts the data for the benzene/ethylene mole ratio of 20:1, curve 9 for the benzene/ethylene mole ratio of 9:1, and curve 10, the curve for the benzene/ethylene mole ratio of 7.9:1. As can be seen by an examination of the data shown in FIG. 2, the catalyst appears completely stable at the benzene/ethylene mole ratios of 10:1 and 7.9:1, and even at the higher ratio of 20:1, the stability was shown to be substantially better than the alumina-binder catalyst at a benzene/ethylene ratio of 10:1. On Day 10 the space velocity of the benzene was reduced and the ethylene flow further reduced to provide a benzene/ethylene ratio of about 3:5, and at this point the catalyst shortly began to show deactivation as indicated by curve 11.

Further experimental work was carried out with a lanthanum beta zeolite with a silica binder (Catalyst B) at mole ratios of benzene/ethylene mole ratios of 20:1 and 10:1 for four successive passes with intervening regenerations. This experimental work was carried out with lanthanum beta having a silica/alumina ratio of 50:1. The temperature was controlled to a maximum of 490° C. with a pressure of 650 psig to operate in the supercritical region, thus providing reaction conditions more severe than the more mild temperature and pressure conditions involved in regular liquid phase alkylation. Each pass was carried out at a LHSV of the benzene feed of 70 hr.$^{-1}$. Between each pass the catalyst was regenerated by the same regeneration procedure as described above.

The results from this experimental work are set forth in Table 1. As indicated Table 1 shows for each pass the EB content, the percent of diethylbenzene as measured against the ethylbenzene in the production stream, the amount of butylbenzene in parts per million based upon the ethylbenzene content, and the amount of propylbenzene in parts per million based upon the ethylbenzene in the product. As can be seen from an examination of Table 1, the catalyst maintained good activity after each regeneration, with the activity of the fourth pass roughly equivalent to the initial activity. In the second regeneration carried out between the second and third passes, an unexpectedly high coke burn caused the temperature of the catalyst bed to exceed the desired maximum temperature of 490° C. for 40 minutes, reaching a high of 550° C. This caused the propylbenzene yields to increase by an order of magnitude as shown in Table 1. However, as is evident from the experimental work described herein, the zeolite beta with silica binder was much more stable and exhibited a substantially better regeneration coefficient than the corresponding zeolite beta with an alumina binder.

TABLE 1

| | La-beta 20/1 ratio Days | | | | 50/1 Sil La-beta 10/1 ratio Days | | 50/1 |
|---|---|---|---|---|---|---|---|
| | 1 | 2 | 3 | 4 | 1 | 2 | 3 |
| EB equivalents | | | | | | | |
| 1$^{st}$ pass | 7.32 | 7.49 | 7.58 | 7.56 | 14.01 | 14.17 | 13.54 |
| 2$^{nd}$ pass | 7.61 | 7.20 | 7.16 | 7.24 | 14.11 | 13.21 | 13.05 |
| 3$^{rd}$ pass | 7.22 | 7.38 | 7.46 | | 13.04 | 13.20 | 14.12 |
| 4$^{th}$ pass | 8.18 | 7.18 | 7.43 | | 14.47 | 13.70 | 13.71 |
| DEB/EB % | | | | | | | |
| 1$^{st}$ pass | 4.61 | 4.9 | 4.96 | 5.01 | 8.23 | 8.21 | 8.11 |
| 2$^{nd}$ pass | 4.61 | 4.47 | 4.44 | 4.64 | 6.53 | 7.24 | 7.71 |
| 3$^{rd}$ pass | 4.2 | 4.3 | 4.34 | | 6.45 | 6.49 | 6.73 |
| 4$^{th}$ pass | 4.53 | 4.29 | 4.31 | | 6.88 | 6.8 | 6.77 |
| Bu-benzenes/ EB eq. (ppm) | | | | | | | |
| 1$^{st}$ pass | 338 | 449 | 470 | 471 | 939 | 942 | 929 |
| 2$^{nd}$ pass | 468 | 426 | 420 | 424 | 1258 | 1050 | 929 |
| 3$^{rd}$ pass | 508 | 510 | 504 | | 1203 | 1211 | 1131 |
| 4$^{th}$ pass | 544 | 538 | 546 | | 1250 | 1200 | 1192 |
| Propyl-benzenes/ EB eq. (ppm) | | | | | | | |
| 1$^{st}$ pass | 189 | 185 | 235 | 429 | 628 | 642 | 608 |
| 2$^{nd}$ pass | 286 | 220 | 208 | 164 | 1949 | 889 | 505 |
| 3$^{rd}$ pass | 2908 | 2683 | 2494 | | 2257 | 2755 | 3309 |
| 4$^{th}$ pass | 7651 | 7270 | 6731 | | 3488 | 3182 | 3088 |

As noted previously, the silica-binder zeolite beta catalysts are designed for use in liquid phase alkylation in accordance with the present invention. In carrying out the invention, the alkylation reaction is carried out at pressures well above the vapor pressure of the aromatic substrate at the reaction temperature involved in order to ensure that a liquid phase is retained throughout the reactor. In order to provide a complete liquid phase reaction, a flooded bed format is used in which the catalyst is completely immersed in liquid. This can readily be accomplished by using an upflow technique such as used in the foregoing experimental work, and this usually will be preferred in carrying out the invention. However, a downflow flooded bed operation can be accomplished by control of the outlet flow rate to ensure that the catalyst beds are covered by liquid benzene or other aromatic substrate.

Figure 3:
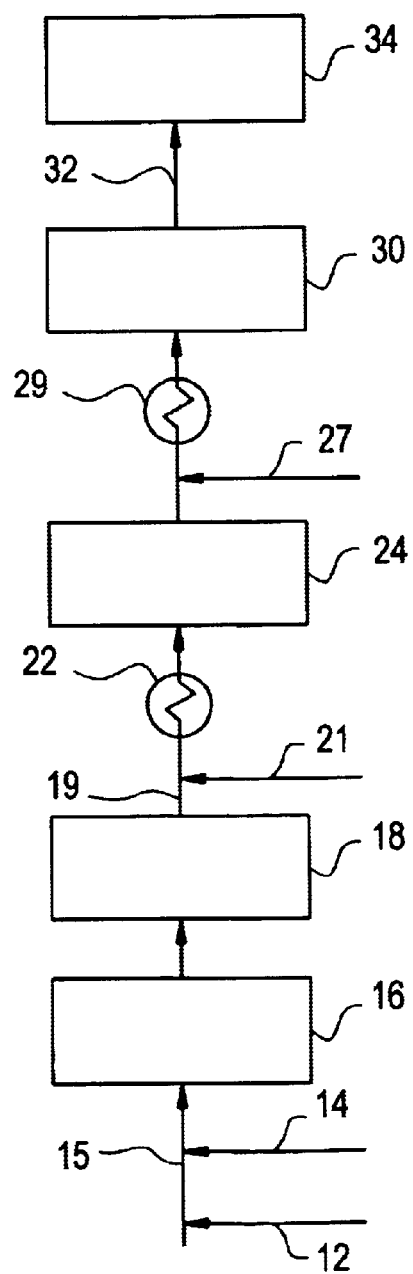
FIG. 3 is a schematic illustration of a staged reactor system which can be used in carrying out the present invention.

Preferably, a staged reaction format is employed in order to ensure good solubility of the ethylene (or other alkylating agent) in the benzene (or other aromatic substrate) and provide that the entire reaction takes place in the liquid phase. The staged reaction format may be provided by a plurality of catalyst beds in a single reactor by a series of sequentially-connected reactors as disclosed in the aforementioned U.S. Pat. No. 5,073,653 to Butler. The provision of multiple stages provides an opportunity for interstage cooling where adiabatic reactors are used or permits the use of several isothermal reaction stages. Turning now to FIG. 3, there is shown a schematic illustration of a staged reactor system used for the production of ethylbenzene by the reaction of ethylene with benzene which includes a plurality of adiabatic reactors with interstage cooling and injection of ethylene. More particularly and as illustrated in the drawing, ethylene and benzene are supplied via lines 12 and 14 to the inlet line 15 of a dehydration unit 16. The dehydration unit functions to dehydrate the input to the alkylation reactors so that it is essentially dry, desirably containing less than 100 ppm water and more preferably less than 50 ppm water. By way of example, dehydrator 16 may take the form of a packed column packed with a desiccant such as silica gel or other suitable hydroscopic medium or an azeotropic crying column.

The dehydrator effluent is supplied to a reactor 18, the first of a plurality of series connected alkylation reactors operated in an upflow mode. Reactor 18 is operated at an average temperature of 350° C. or less and preferably at an average temperature within the range of 150°–250° C. For liquid phase operation, the pressure on reactor 18 is sufficient to maintain the benzene in the liquid phase and preferably is at least 50 psi above the vapor pressure of the benzene at the reactor temperature. Typically, the reactor pressure is within the range of about 500–850 psia. The remaining downstream reactors normally are operated under approximately the same conditions as the initial reactor. The effluent from the initial reactor 18 is withdrawn via line 19 and applied through a heat exchanger 22 where it is cooled prior to being supplied to the second stage reactor 24. Ethylene is supplied via line 21 where it is mixed with the effluent from the first reactor 18. Preferably, the ethylene is supplied to the reactor effluent prior to cooling as shown in the drawing in order to facilitate distribution of the ethylene throughout the liquid benzene. Desirably, the cooling step is carried out to reduce the temperature of the feed mixture supplied to the second reactor 24 to a value about the same as the inlet temperature to the first reactor 18. The average temperature in the second reactor normally will be about the same as that of the first reactor. The pressure will of necessity be somewhat lower in order to provide for sufficient pressure gradient to accommodate flow through the system. The effluent from the second reactor 24 is supplied along with ethylene provided via line 27 to a second interstage cooling unit 29 where the charge mixture to third reactor 30 is again cooled to a temperature about equal to the inlet temperature for the first two reactors.

The output from reactor 30 is supplied via line 32 to a down-stream separation and processing unit 34. In unit 34, ethylbenzene is separated and withdrawn as the product of the alkylation plant. Typically, ethylbenzene will be used as the charge to a dehydrogenation system where it undergoes catalytic dehydrogenation in the production of styrene. Normally, benzene and ethylene will be separated in unit 34 and recycled for use in the alkylation process. Heavier polyethylbenzenes may be transalkylated with benzene to produce additional ethylbenzene. A suitable multistage separation system together with a transalkylation system may take the form of one of the integrated systems disclosed in the aforementioned EPA 467,007, the entire disclosure of which is incorporated herein by reference. Stoichiometric excess of benzene to ethylene will be supplied in the charge stock to the alkylation reactors in order to enhance selectivity for monoalkylation. Operation of the reactors to provide liquid phase alkylation under relatively mild conditions not only minimizes the xylene produced in the alkylation reaction but also enables the use of a somewhat lower benzene/ethylene molar ratio than is usually the case. Benzene/ethylene molar ratios as low as about 2:1 may be employed, although ratios of about 4:1 usually will be used. However, there is usually little incentive to use extremely high ratios, and as a practical matter, the benzene/ethylene molar ratio will seldom exceed 15:1. Preferred benzene/ethylene mole ratios are about 4/1. The benzene/ethylene mole ratios referred to above are with respect to the overall system, and for a multi-stage reaction system, such as depicted in the drawing, the benzene/ethylene ratio of the feed to each stage will be less than the overall ratio. The amount of ethylene solubilized in the benzene charge to each reactor stage will depend in part upon the number of reactor stages employed. Normally, at least three reactor stages, as illustrated, will be used. Additional reactor stages will be provided although the total number of stages normally will not exceed 8. Preferably, the pressure in each reaction stage and the amount of ethylene supplied therein is such as to provide at least 1 mole percent of ethylene solubilized in the benzene. Usually, at least 2 mole percent of ethylene will be solubilized in the charge to each reactor. Unless a great many reactor stages are employed, usually the amount of ethylene solubilized in the liquid benzene phase of each reactor will be at least 4 mole percent.

Multistage ethylation of benzene may also be carried out in accordance with the present invention employing isothermal reaction zones. Isothermal reactors can take the form of shell and tube type heat exchangers with the alkylation catalyst deposited within the tubes and with a heat transfer medium circulated through the shell surrounding the catalyst-filled tubes. The heat exchange medium will of course be supplied through the reactors at rates to maintain a relatively constant temperature across each reaction stage. In this case interstage cooling will be unnecessary although it will be preferred to inject ethylene at the front of each reaction stage.

As noted previously, it is preferred to use the beta-silica catalyst in liquid phase alkylation reaction under relatively mild conditions. However, the present invention can be carried out with an alkylation reactor operated in a quasi-liquid phase with the benzene substrate under more severe conditions in which both the temperature and the pressure are above the critical temperature and pressure for benzene to operate in the supercritical region. As noted previously, in this case the alkylation reactor would be operated at a temperature of about 290° or above and a pressure in excess of 700 psia. Somewhat higher temperatures and pressures would normally be employed. Here, operation of the alkylation reactor with benzene in the supercritical region would be within the range of 300–600° C. and about 650–850 psia.

Having described specific embodiments of the present invention, it will be understood that modifications thereof may be suggested to those skilled in the art, and it is intended to cover all such modifications as fall within the scope of the appended claims.

What is claimed:

1. In the production of ethylbenzene the method comprising:

(a) supplying a feed stock containing benzene into a reaction zone and into contact with a molecular sieve catalyst comprising a zeolite beta alkylation catalyst formulated with a silica binder;

(b) supplying ethylene to said reaction zone;

(c) operating said reaction zone at temperature and pressure conditions in which benzene is in the liquid phase or in the supercritical phase to cause ethylation of said benzene in the presence of said alkylation catalyst at a primary activity;

(d) recovering an alkylation product containing ethylbenzene from said reaction zone;

(e) continuing the operation of said reaction zone until the activity of said catalyst for the ethylation of benzene decreases by a value of at least 0.1% from the primary activity of said catalyst for the ethylation of benzene;

(f) terminating the operation of said reaction zone for the alkylation of benzene and instituting a regeneration procedure in which said catalyst is regenerated in an oxidizing environment at a average temperature in the course of said regeneration procedure of less than 500° C., (g) subsequent to said regeneration procedure, reinstituting the operation of said alkylation reaction zone by supplying benzene to said alkylation reaction zone containing said regenerated catalyst (h) operating said reaction zone at temperature arid pressure conditions effective to cause the ethylation of said benzene in the liquid phase or in the supercritical phase to cause ethylation of said benzene in the presence of said regenerated catalyst to produce ethylbenzene at a secondary activity of at least 95% of the primary activity, (i) continuing the operation of said alkylation reaction zone until the activity of said catalyst for the ethylation of benzene declines by an amount of at least 0.1% of the secondary activity;

(j) terminating the operation of the alkylation reaction zone and secondly regenerating said catalyst in an oxidizing environment and at an average temperature of less than 500° C. to effect a regeneration of said catalyst, (k) supplying benzene and ethylene to said alkylation reaction zone containing said secondly regenerated catalyst;

(l) operating said reaction zone at temperature and pressure conditions effective to cause the ethylation of benzene in liquid phase or in the supercritical phase to cause ethylation of said benzene in the presence of said regenerated catalyst to provide an initial tertiary activity for the ethylation of benzene of at least 95% of the secondary activity;

(m) continuing the operation of said alkylation reaction zone until the activity of said regenerated catalyst for the ethylation of benzene declines by an amount of at least 0.1% of the tertiary activity;

(n) terminating the operation of said alkylation reaction zone and thirdly regenerating said catalyst in an oxidizing environment and at an average temperature of less than 500° C. to effect a third regeneration of said catalyst;

(o) supplying benzene and ethylene to said alkylation reaction zone containing said thirdly regenerated catalyst; and (p) operating said reaction zone at temperature and pressure conditions effective to cause the ethylation of benzene in liquid phase or in the supercritical phase to cause ethylation of said benzene in the presence of said regenerated catalyst to provide a quaternary activity for the ethylation of benzene of at least 95% of the tertiary activity wherein said zeolite beta exhibits a regeneration coefficient at the conclusion of at least three regenerations which is at least 105% of the value of the regeneration coefficient of the zeolite beta catalyst formulated with an aluminum binder in the same amount as the silica binder employed with the zeolite beta, wherein the zeolite beta alkylation catalyst formulated with a silica binder comprises a lanthanum-modified zeolite beta in which lanthanum ions are incorporated by ion exchange into the zeolite beta.

2. The method of claim 1 wherein said reaction zone is operated at temperature and pressure conditions at which said benzene is in the liquid phase.

3. The method of claim 2 wherein said benzene and ethylene are supplied to said reaction zone at flow rates to provide a mole ratio of benzene to said alkylating agent of less than 15.

4. The method of claim 3 wherein the mole ratio of said benzene to said ethylene is less than 10.

5. The method of claim 3 wherein the mole ratio of benzene to said alkylating agent is within the range of 4–10.

6. The method of claim 1 wherein said modified zeolite beta comprises a modified zeolite beta having an intergrowth of a ZSM-12 crystalline framework within the crystalline structure of the zeolite beta.

7. The method of claim 1 wherein said zeolite beta has a silicia/aluminum ratio of at least 40.

8. In the production of etbylbenzene the method comprising:

(a) supplying a feed stock containing benzene into a reaction zone and into contact with a molecular sieve catalyst comprising a zeolite beta alkylation catalyst formulated with a silica binder;

(b) supplying ethylene to said reaction zone;

(c) operating said reaction zone at temperature and pressure conditions in which benzene is in the supercritical phase to cause ethylation of said benzene in the presence of said alkylation catalyst at a primary activity;

(d) recovering an alkylation product containing ethylbenzene from said reaction zone;

(e) continuing the operation of said reaction zone until the activity of said catalyst for the ethylation of benzene decreases by a value of at least 0.1% from the primary activity of said catalyst for the ethylation of benzene;

(f) terminating the operation of said reaction zone for the alkylation of benzene and instituting a regeneration procedure in which said catalyst is regenerated in an oxidizing environment at a average temperature in the course of said regeneration procedure of less than 500° C.;

(g) subsequent to said regeneration procedure, reinstituting the operation of said alkylation reaction zone by supplying benzene to said alkylation reaction zone containing said regenerated catalyst;

(h) operating said reaction zone at temperature and pressure conditions effective to cause the ethylation of said benzene in the supercritical phase to cause ethylation of said benzene in the presence of said regenerated catalyst to produce ethylbenzene at a secondary activity of at least 95% of the primary activity;

(i) continuing the operation of said alkylation reaction zone until the activity of said catalyst for the ethylation of benzene declines by an amount of at least 0.1% of the secondary activity;

(j) terminating the operation of the alkylation reaction zone and secondly regenerating said catalyst in an oxidizing environment and at an average temperature of less than 500° C. to effect a regeneration of said catalyst;

(k) supplying benzene and ethylene to said alkylation reaction zone containing said secondly regenerated catalyst;

(l) operating said reaction zone at temperature and pressure conditions effective to cause the ethylation of benzene in the supercritical phase to cause ethylation of said benzene in the presence of said regenerated catalyst to provide an initial tertiary activity for the ethylation of benzene of at least 95% of the secondary activity;

(m) continuing the operation of said alkylation reaction zone until the activity of said regenerated catalyst for the ethylation of benzene declines by an amount of at least 0.1% of the tertiary activity;

(n) terminating the operation of said alkylation reaction zone and thirdly regenerating said catalyst in an oxidizing environment and at an average temperature of less than 500° C. to effect a third regeneration of said catalyst;

(o) supplying benzene and ethylene to said alkylation reaction zone containing said thirdly regenerated catalyst; and (p) operating said reaction zone at temperature and pressure conditions effective to cause the ethylation of benzene in liquid phase or in the supercritical phase to cause ethylation of said benzene in the presence of said regenerated catalyst to provide a quaternary activity for the ethylation of benzene of at least 95% of the tertiary activity wherein said zeolite beta exhibits a regeneration coefficient at the conclusion of at least three regenerations which is at least 105% of the value of the regeneration coefficient of the zeolite beta catalyst formulated with an alumina binder in the same amount as the silica binder employed with the zeolite beta, wherein the zeolite beta alkylation catalyst formulated with a silica binder comprises a lanthanum-modified zeolite beta in which lanthanum ions are incorporated by ion exchange into the zeolite beta.

* * * * *